United States Patent
Watanabe et al.

(10) Patent No.: US 7,905,834 B2
(45) Date of Patent: Mar. 15, 2011

(54) REMOTE ULTRASONIC DIAGNOSTIC SUBJECT-SIDE APPARATUS, REMOTE ULTRASONIC DIAGNOSTIC EXAMINER-SIDE APPARATUS AND REMOTE ULTRASONIC DIAGNOSTIC SYSTEM

(75) Inventors: Yoshinobu Watanabe, Kadoma (JP); Hisashi Hagiwara, Kanagawa (JP); Yoshinao Tannaka, Kanagawa (JP); Takao Suzuki, Kanagawa (JP)

(73) Assignee: Panasonic Corporation, Osaka (JP)

( * ) Notice: Subject to any disclaimer, the term of this patent is extended or adjusted under 35 U.S.C. 154(b) by 748 days.

(21) Appl. No.: 10/597,660

(22) PCT Filed: Feb. 2, 2005

(86) PCT No.: PCT/JP2005/001464
§ 371 (c)(1),
(2), (4) Date: Aug. 2, 2006

(87) PCT Pub. No.: WO2005/074808
PCT Pub. Date: Aug. 18, 2005

(65) Prior Publication Data
US 2008/0249401 A1    Oct. 9, 2008

(30) Foreign Application Priority Data

Feb. 3, 2004  (JP) ................................ 2004-027206
Feb. 3, 2004  (JP) ................................ 2004-027207

(51) Int. Cl.
*A61B 8/00* (2006.01)
(52) U.S. Cl. ...................................................... 600/437
(58) Field of Classification Search .................. 600/437
See application file for complete search history.

(56) References Cited

U.S. PATENT DOCUMENTS

| 5,938,607 A | 8/1999 | Jago et al. |
| 6,565,510 B1 * | 5/2003 | Haider ........................... 600/437 |
| 2003/0067903 A1 * | 4/2003 | Jorgensen ..................... 370/338 |
| 2003/0083563 A1 * | 5/2003 | Katsman et al. .............. 600/407 |

(Continued)

FOREIGN PATENT DOCUMENTS

JP    2000-175870    6/2000

(Continued)

OTHER PUBLICATIONS

H. Yagi et al., "The Ultrasound Image Transfer in Remote Diagnosis", The Japan Society of Ultrasonics in Medicine Kiso Gijyutsu Kenkyu bukai Shiryo, Apr. 25, 1997, vol. 97, No. 1, pp. 39-43 (Partial English Translation).

(Continued)

*Primary Examiner* — Eric F Winakur
*Assistant Examiner* — Hien Nguyen
(74) *Attorney, Agent, or Firm* — Hamre, Schumann, Mueller & Larson, P.C.

(57) ABSTRACT

A subject-side apparatus 10A is provided with a cine memory 15 for sequentially storing an ultrasonic signal that is received by an ultrasonic wave transmission/reception portion 12 per each frame. Every time after freezing when moving a pointer for designating a frame to be reproduced in a hospital-side apparatus 20A, a communication line interface 14 of the subject-side apparatus reproduces a frame that is required to be retransmitted by a console 24 of the hospital-side apparatus from the cine memory, and retransmits it to a communication line interface 21 of the hospital-side apparatus via a communication line 30. Then, an ultrasonic image of the retransmitted frame is displayed on a monitor 23. When an examiner performs a diagnosis with respect to a subject in a remote location via the communication line, an ultrasonic image can be displayed with sufficiently suppressed degradation of an image quality compared with an image quality of an original image, even at a low data rate of the communication line.

6 Claims, 11 Drawing Sheets

U.S. PATENT DOCUMENTS

2003/0195424 A1* 10/2003 McMorrow et al. .......... 600/439
2004/0153862 A1* 8/2004 Grellmann et al. ............. 714/43

FOREIGN PATENT DOCUMENTS

| JP | 2001-175793 | 6/2001 |
| JP | 2002-17732 | 1/2002 |
| JP | 2002-282251 | 10/2002 |
| JP | 2002282251 | * 10/2002 |

OTHER PUBLICATIONS

Y. Shimizu, "The Prototyping of the Ultrasound Remote Diagnosis System and Attempts of the image transfer and Remote Control through the Internet", Journal of Medical Ultrasonics, Nov. 15, 2003, vol. 30, No. 6, pp. J773 (Full English Translation).

* cited by examiner

REMOTE ULTRASONIC DIAGNOSTIC SUBJECT-SIDE APPARATUS, REMOTE ULTRASONIC DIAGNOSTIC EXAMINER-SIDE APPARATUS AND REMOTE ULTRASONIC DIAGNOSTIC SYSTEM

TECHNICAL FIELD

The present invention relates to a ultrasonic diagnostic system for medical use, and particularly relates to a remote ultrasonic diagnostic system that is capable of providing an ultrasonic image by which an examiner can perform a diagnosis, even when a subject being examined is physically remote from the examiner (medical doctor in a hospital).

BACKGROUND ART

According to reduction in size of an ultrasonic diagnostic apparatus that easily provides a tomographic image of a subject as a real-time ultrasonic dynamic image, the ultrasonic diagnostic apparatus plays more important roles in various medical diagnoses and examinations at the places other than ultrasonic inspection rooms, such as bedsides in hospital wards, private clinics and health care support center in the offices, for example.

However, because of the limitation of the number of medical doctors as examiners who can perform diagnoses accurately from displayed ultrasonic dynamic images, the shortage of the medical doctors who can interpret ultrasonic images would be of concern in the case where the ultrasonic diagnostic apparatuses become prevalent as the demand for apparatuses for home medical care is expected to grow in the market in the future.

In addition, as speeds of communication networks represented by internets are increased, connections via communication lines have become possible in various fields. There is an expectation for the development of an ultrasonic diagnostic apparatus enabling a remote diagnosis that is connected to a hospital via a communication line, and can enable a medical doctor in the hospital to perform an accurate diagnosis, even when such a medical doctor is not present near the patient, for example, in the case where the acute patient is in, for example, an aircraft in flight, a watercraft under sail, a running train or the like, or in the case where the injured person is carried with an ambulance. As such an ultrasonic diagnostic apparatus, a remote ultrasonic diagnostic system utilizing a communication line (see, for example, Patent document 1) and the like are known.

As mentioned above, in recent years, a data rate that can be transmitted through a communication line such as an internet has been dramatically increased in speed, but has not reached a speed that enables transmission of an uncompressed real-time ultrasonic dynamic image generated by an ultrasonic diagnostic apparatus. Thus, in the above-described conventional example, transmission of the real-time ultrasonic dynamic image is performed by introducing a high-efficiency data compression method such as MPEG that can compress image information to have the data rate at an upper limit value or less of the communication line, and can suppress deterioration of an image to a minimum, thus making efforts to transmit a real-time ultrasonic dynamic image that is dose to the original image even when the data rate of the line is low.

In the remote ultrasonic diagnostic system, a hospital-side apparatus that receives an ultrasonic image is required to exclude factors that may affect a medical diagnosis negatively, such as degradation in image quality, a decrease in image size and a decrease in frame rate due to a speed of the communication line.

Patent document 1: JP 2002-17732 A

DISCLOSURE OF INVENTION

Problem to be Solved by the Invention

However, it is very rare that the data rate of the communication line can be secured stably over a long period of time, and in the case where the data rate of the communication line is not enough, measures for coinciding a timing of receiving the image with a real time are taken, by reducing frames of the reception side (or the transmission side) so that, for example, the reception side has a frame rate of 15 frames/second even when the original image has a frame rate of 30 frames/second.

In addition, in an ultrasonic diagnosis in a clinical setting, there are frequent cases where, after performing a diagnosis by using an ultrasonic dynamic image in real time, the image is frozen once, and diagnostic contents are confirmed again by using a cine-memory function for reproducing image data that are accumulated in a memory inside the apparatus, and are output to a recording device. Moreover, there is a problem that, in a diagnosis of a circulatory system such as a heart, for example, only reproducing an image of 15 frames/second with frames reduced from the original image of 30 frames/second cannot provide necessary and sufficient image information to an examiner (medical doctor).

Furthermore, in order to compress data, hardware (or high-speed processing software) designed specifically for data compression is required, and a time lag occurs depending on the image compression method, where there is a general trend that a higher compression rate provides a larger time lag. Thereby, a medical doctor performing an examination at a remote location may be frustrated, which may deteriorate the diagnosis efficiency. In addition, since the image information is compressed by a compression method that has a high efficiency but is irreversible, there is a problem in that an image quality of an ultrasonic image displayed on the hospital-side apparatus is inevitably lower than that of the original image.

The present invention was made in view of the above-described conventional problems, and it is an object of the present invention to provide a remote ultrasonic diagnostic system that can display an ultrasonic image with sufficiently suppressed degradation of an image quality compared with an image quality of an original image, even at a low data rate of a communication line, when an examiner performs a diagnosis with respect to a subject in a remote location via the communication line.

Means for Solving a Problem

The present invention is based on a remote ultrasonic diagnostic system including: an examiner-side apparatus by which an examiner performs a diagnosis with respect to a subject in a remote location via a communication line by using an ultrasonic image; and a subject-side apparatus on the subject side.

In order to attain the above-described object, a first subject-side apparatus of the present invention includes: an ultrasonic wave transmission/reception portion for receiving an ultrasonic echo that is generated from an electroacoustic converting means driven by a transmission pulse, and receiving an ultrasonic echo reflected by an inside of the subject; an image generation portion for generating ultrasonic image data from an ultrasonic signal that is received by the ultrasonic wave transmission/reception portion; a cine memory for sequentially storing the ultrasonic signal that is received by the ultrasonic wave transmission/reception portion per each frame; and a communication line interface for reproducing, from the cine memory, the frame that is requested to be retransmitted by the examiner-side apparatus after freezing, and retransmitting the frame to the examiner-side apparatus via the communication line.

In addition, a first examiner-side apparatus of the present invention includes: a communication line interface for requesting a communication line interface of the subject-side apparatus to retransmit a frame to be reproduced so as to retransmit the frame via the communication line, every time after freezing when moving a pointer for designating the frame to be reproduced from a cine memory that sequentially stores an ultrasonic signal received by an ultrasonic wave transmission/reception portion of the subject-side apparatus per each frame; an image formation portion for forming an ultrasonic image of the retransmitted frame; and a displaying means for displaying the ultrasonic image that is formed by the image formation portion.

In addition, a first remote ultrasonic diagnostic system of the present invention has a configuration where the first subject-side apparatus and the first remote ultrasonic diagnostic examiner-side apparatus are connected via a communication line.

According to this configuration, the subject-side apparatus is provided with a cine-memory function, and thus retransmits an image that is designated by the pointer from the subject-side apparatus, every time when the frame pointer is moved for the purpose of cine-memory reproduction in the examiner-side (hospital-side) apparatus, after the hospital-side apparatus is frozen. Thereby, even when frames are missing intermittently due to an insufficient speed of the communication line in a live mode, and when a plurality of frames are missing continuously due to a failure of the communication line, the hospital-side apparatus can perform cine-memory reproduction and display with no missing frame after the freezing.

In the first remote ultrasonic diagnostic system, it is preferable that the communication line interface of the subject-side apparatus retransmits at least a part of all frames that are accumulated in the cine memory of the subject-side apparatus to the examiner-side apparatus in a background, after freezing, and the examiner-side apparatus includes the cine memory for storing an ultrasonic image of the frame that is retransmitted after the freezing.

According to this configuration, the hospital-side apparatus is provided with a cine-memory function, and the hospital-side apparatus receives (for example, in the background) information that is accumulated in the cine memory of the subject-side apparatus from the time of the freezing, and accumulates the information in the cine memory of the hospital-side apparatus. Thereby, even when the communication line between the subject side and the hospital side is disconnected due to a deterioration of a condition of the line, the hospital-side apparatus alone can continue a diagnosis by the cine-memory reproduction and display with no missing frame.

In the first remote ultrasonic diagnostic system, it is preferable that the subject-side apparatus includes a displaying means for displaying an ultrasonic image that is retransmitted to the examiner-side apparatus.

According to this configuration, when the frame that is requested to be retransmitted by the hospital-side apparatus is retransmitted to the hospital-side apparatus, if the frame also is displayed on a second displaying means of the subject-side apparatus, (an operator on) the subject side and (a medical doctor on) the hospital side can share diagnostic information by the same image.

In order to attain the above-described object, a second subject-side apparatus of the present invention includes: an ultrasonic wave transmission/reception portion for transmitting an ultrasonic echo that is generated from an electroacoustic converting means driven by a transmission pulse, and receiving an ultrasonic echo reflected by an inside of the subject; an image generation portion for generating ultrasonic image data from an ultrasonic signal that is received by the ultrasonic wave transmission/reception portion; a cine memory for sequentially storing the ultrasonic signal that is received by the ultrasonic wave transmission/reception portion per each frame; a displaying means for reproducing, from the cine memory, the frame that is requested to be retransmitted in the subject-side apparatus after freezing, and displaying the frame as an ultrasonic image; and a communication line interface for retransmitting the frame that corresponds to the ultrasonic image displayed on the displaying means to the examiner-side apparatus via the communication line.

In addition, a second examiner-side apparatus includes: a communication line interface for receiving a frame that is retransmitted from a communication line interface of the subject-side apparatus via the communication line, after freezing; an image formation portion for forming an ultrasonic image of the retransmitted frame; and a displaying means for displaying the ultrasonic image that is formed by the image formation portion.

In addition, a second remote ultrasonic diagnostic system of the present invention has a configuration where the second subject-side apparatus and the second examiner-side apparatus are connected via a communication line.

According to this configuration, when the subject-side apparatus reproduces and displays on the displaying means of the subject-side apparatus by using the reproduction function from the cine memory, if the displayed frame is retransmitted also to the hospital-side apparatus, (an operator on) the subject side and (a medical doctor on) the hospital side can share diagnostic information by the same image, similarly to a third remote ultrasonic diagnostic system.

In order to attain the above-described object, a third subject-side apparatus of the present invention includes: an ultrasonic wave transmission/reception portion for transmitting an ultrasonic echo that is generated from an electroacoustic converting means driven by a transmission pulse, and receiving an ultrasonic echo reflected by an inside of the subject; an image generation portion for generating ultrasonic image data by performing a filtering process with respect to an ultrasonic signal that is received by the ultrasonic wave transmission/reception portion; and a communication line interface for transmitting the ultrasonic image data that is generated by the image generation portion to the examiner-side apparatus via the communication line.

In addition, a third examiner-side apparatus of the present invention includes: a communication line interface for receiving an ultrasonic image data that is transmitted from a communication line interface of the subject-side apparatus via the communication line; a scan converting means for converting the number of scanning lines of the received ultrasonic image data; and a displaying means for displaying the ultrasonic image data that is scanned and converted by the scan converting means.

In addition, the third remote ultrasonic diagnostic system has a configuration where the third subject-side apparatus and the third examiner-side apparatus are connected via a communication line.

According to this configuration, considering the ultrasonic image data at the time immediately before being input into the scan converting means of the hospital-side apparatus, which has the lowest data rate in a circuit inside the examiner-side (hospital-side) apparatus in the remote ultrasonic diagnostic system, the image generation portion performs the filtering process (or a resampling process) so as to optimize the ultrasonic image data for the scan converter of the hospital-side apparatus, the optimized image data is transmitted directly to the communication line, and, in the hospital-side apparatus, the scan converting means converts the number of scanning lines of the ultrasonic image data that is received via the communication line so as to display the image. Thereby, a real-time ultrasonic dynamic image that does not require any special image compressing means and thus does not generate any time lag due to the compression can be transmitted/received.

In the third remote ultrasonic diagnostic system, it is preferable that the displaying means of the examiner-side apparatus displays, as a real-time ultrasonic dynamic image, a real-time ultrasonic dynamic image that is transmitted from the subject-side apparatus.

According to this configuration, since the original image data can be transmitted in real time at a data rate that is equivalent or lower than a data rate in the case of using a high-compression-rate image compressing means, the hospital-side apparatus that is connected with the subject-side apparatus via the communication line can receive the real-time ultrasonic dynamic image without any degradation in image quality from the original image.

In addition, in this remote ultrasonic diagnostic system, it is preferable that the subject-side apparatus includes: a scan converting means for converting the number of scanning lines of the ultrasonic image data that is generated from the image generation portion; and a displaying means for displaying the ultrasonic image data that is scanned and converted by the scan converting means.

According to this configuration, the subject-side apparatus also is provided with the scan converter, and thus can display, as the real-time ultrasonic dynamic image, an image that is the same as the image displayed on the hospital-side apparatus, whereby (an operator on) the subject side and (a medical doctor on) the hospital side can share diagnostic information.

In order to attain the above-described object, a fourth subject-side apparatus of the present invention includes: an ultrasonic wave transmission/reception portion for transmitting an ultrasonic echo that is generated from an electroacoustic converting means driven by a transmission pulse, and receiving an ultrasonic echo reflected by an inside of the subject; an image generation portion for generating ultrasonic image data by performing a filtering process with respect to an ultrasonic signal that is received by the ultrasonic wave transmission/reception portion; a cine memory for sequentially storing the ultrasonic signal that is received by the ultrasonic wave transmission/reception portion per each frame; and a communication line interface for reproducing, from the cine memory, the frame that is requested to be retransmitted by the examiner-side apparatus after freezing, and retransmitting the frame to the examiner-side apparatus via the communication line.

In addition, a fourth examiner-side apparatus of the present invention includes: a communication line interface for requesting a communication line interface of the subject-side apparatus to retransmit a frame to be reproduced and retransmitting the frame via the communication line, every time after freezing when moving a pointer for designating the frame to be reproduced from a cine memory that sequentially stores an ultrasonic signal received by an ultrasonic wave transmission/reception portion of the subject-side apparatus per each frame; an image formation portion that includes a scan converting means for converting the number of scanning lines of an ultrasonic image data of the retransmitted frame, and forms an ultrasonic image by the scan converting means; and a displaying means for displaying the ultrasonic image that is formed by the image formation portion.

In addition, the fourth remote ultrasonic diagnostic system of the present invention has a configuration where the fourth subject-side apparatus and the fourth examiner-side apparatus are connected via a communication line.

EFFECTS OF THE INVENTION

According to the remote ultrasonic diagnostic system of the present invention, when an examiner performs a diagnosis with respect to a subject in a remote location via a communication line, an ultrasonic image with sufficiently suppressed degradation of an image quality compared with an image quality of an original image can be displayed, even with a low data rate of the communication line.

Figure 1:
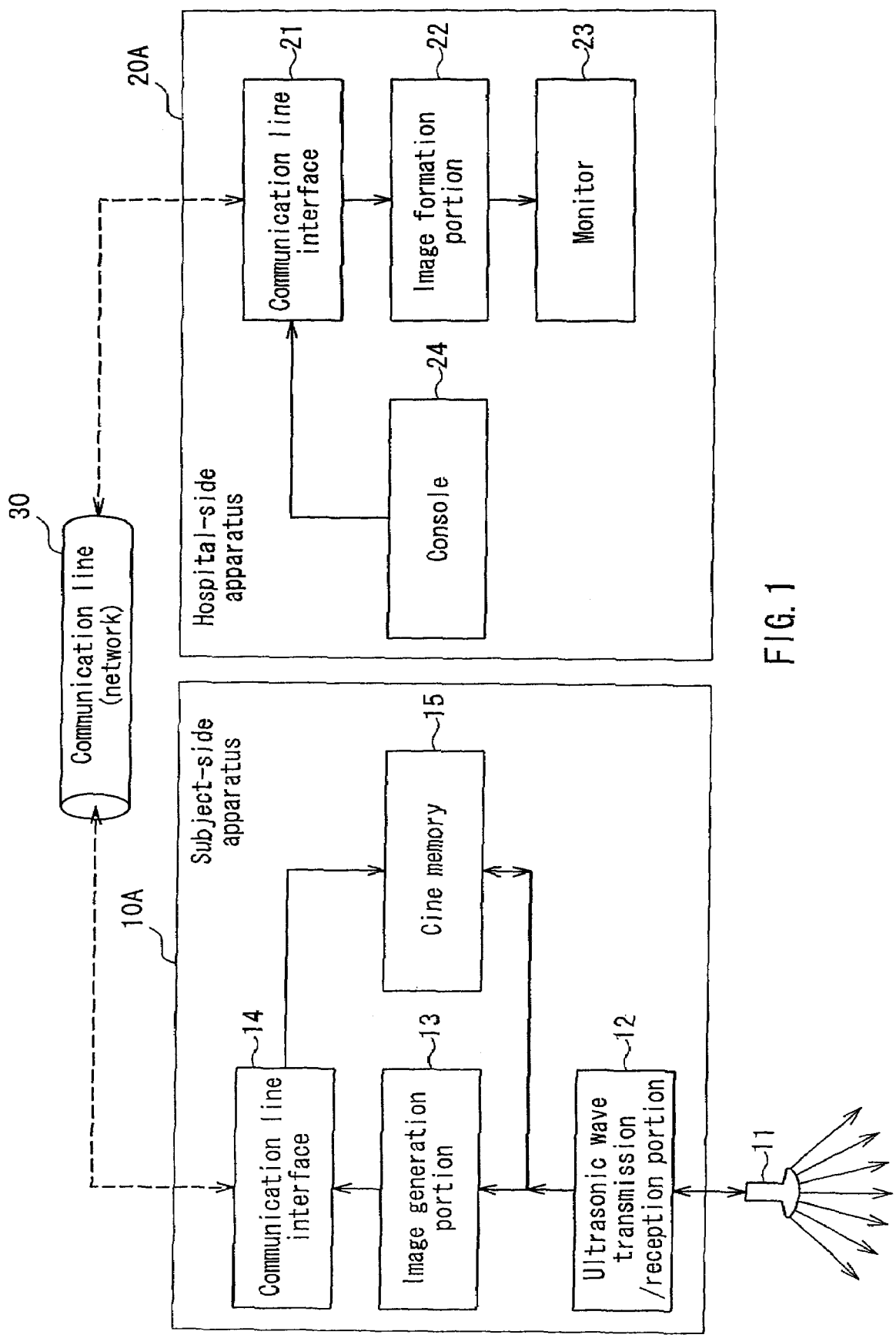
FIG. 1 is a block diagram schematically showing an example of a configuration of a remote ultrasonic diagnostic system according to Embodiment 1 of the present invention.

EXPLANATION OF REFERENCE CODES 10A, 10B, 10C, 10D, 10E, 10F subject-side apparatus
11 ultrasonic probe 12 ultrasonic wave transmission/reception portion
13 image generation portion
14 communication line interface
15 cine memory
16 monitor
17 console
18 image generation portion
20A, 20B, 20C, 20D, 20E hospital-side apparatus
21 communication line interface
22 image formation portion
23, 26 monitor
24 console
25 cine memory
27 scan converter
30 communication line
40, 41 personal computer

DESCRIPTION OF THE INVENTION

Preferable embodiments of the present invention will be described below in detail, with reference to the drawings.

Embodiment 1

FIG. 1 is a block diagram schematically showing an example of a configuration of a remote ultrasonic diagnostic system according to Embodiment 1 of the present invention. A transmission pulse generated by an ultrasonic wave transmission/reception portion 12 in a subject-side apparatus 10A drives an ultrasonic probe 11 (electroacoustic converting means) that is connected to the subject-side apparatus 10A, and an ultrasonic signal is transmitted from the ultrasonic probe 11 into the subject and starts to receive the signal at the same time. The received ultrasonic signal is subjected to delay synthesis at the ultrasonic wave transmission/reception portion 12, and an ultrasonic image data is generated at an image generation portion 13. Moreover, an input signal to the image generation portion 13 is input also into a cine memory 15 (cine memory of the subject-side apparatus), and the cine memory 15 sequentially stores a reception signal as image information per each frame from the ultrasonic wave transmission/reception portion 12.

Image data that is generated at the image generation portion 13 is transmitted from a communication line interface 14 (communication line interface of the subject-side apparatus) to a communication line (network) 30 such as an internet and a LAN. In a hospital-side apparatus 20A (examiner-side apparatus), a communication line interface 21 (communication line interface of the examiner-side apparatus) receives the image data that is transmitted from the subject-side apparatus 10A via the communication line 30, transmits the image data to an image formation portion 22, and finally displays an ultrasonic image on a monitor 23 (displaying means of the examiner-side apparatus).

Figure 2:
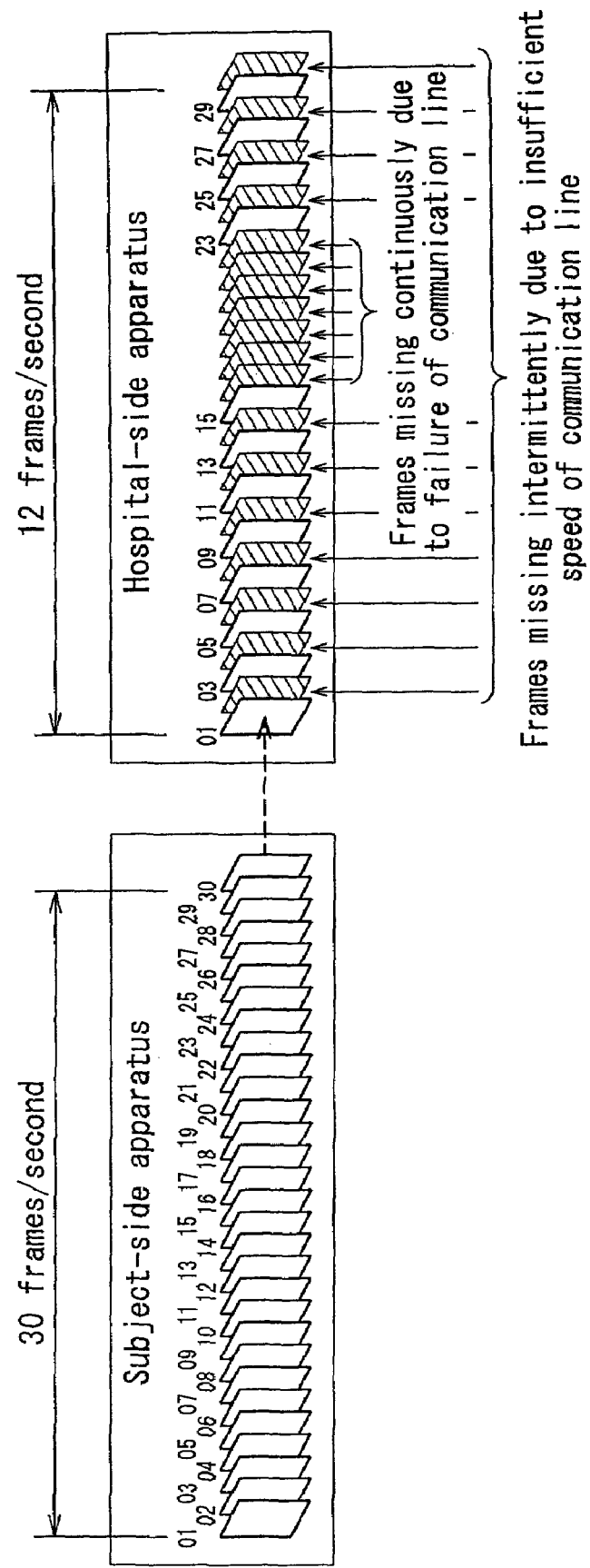
FIG. 2 is a schematic diagram showing a state of missing frames depending on the condition of a communication line.

Herein, as shown in FIG. 2, in the case where a data rate of the communication line is not sufficient when the subject-side apparatus 10A transmits the image data of 30 frames/second to the hospital-side apparatus 20A, some of the frames that can be received by the hospital-side apparatus 20A are missing intermittently. For example, in the case where only a half of the data rate can be secured, frames are missing at a rate of 15 frames/second. Furthermore, if any failure of the communication line occurs additionally, a plurality of frames may be missing continuously.

Figure 3:
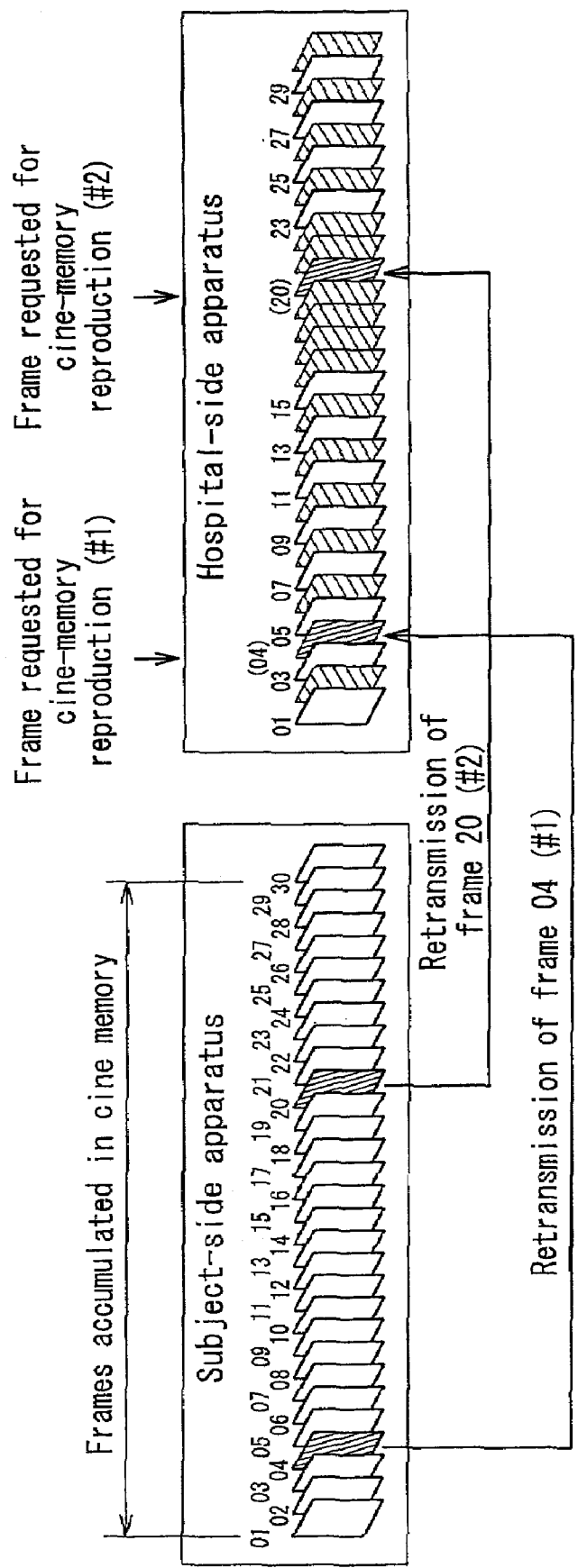
FIG. 3 is a schematic diagram showing a state of retransmitting a frame that is requested to be reproduced by a cine memory.

In an actual scene of an ultrasonic diagnosis, there are frequent cases where, after performing a diagnosis by using an ultrasonic image in a live mode in real time, the image is frozen once, and the diagnostic data are confirmed again by using a cine-memory function for reproducing frames of image data that are accumulated in a memory inside the apparatus, and are output to a recording device. However, as shown in FIG. 2, most frames are missing and only 12 frames of the image data in one second reach the hospital-side apparatus 20A after the freezing. Therefore, in the case where a console 24 requests cine-memory reproduction with respect to, for example, a frame "04" or a frame "20", the subject-side apparatus 10A automatically retransmits a designated frame as shown in FIG. 3, and the frame is displayed on the monitor 23 of the hospital-side apparatus 20A.

In this case, since it is after the freezing, even if a speed of the communication line is insufficient for transmitting/receiving the ultrasonic image in a live mode in real time, one frame of the image data that is requested to perform frame reproduction by the cine-memory function can be transmitted/received. Thereby, an operator (medical doctor) using the hospital-side apparatus 20A can perform a diagnosis by the cine-memory reproduction without any frame missing from all of the 30 frames that are obtained by the subject-side apparatus 10A per one second.

As mentioned above, the present embodiment can provide the excellent remote ultrasonic diagnostic system, in which the subject-side apparatus 10A is provided with the cine-memory function, and retransmits an image that is designated by the pointer from the subject-side apparatus 10A, each time when the frame pointer is moved for the purpose of the cine-memory reproduction in the hospital-side apparatus 20A, after the hospital-side apparatus 20A is frozen. Thereby, even when frames are missing intermittently due to an insufficient speed of the communication line in a live mode, and when a plurality of frames are missing continuously due to a failure of the communication line, the hospital-side apparatus 20A can perform the cine-memory reproduction and display with no missing frame after the freezing.

In addition, as the hospital-side apparatus 20A, a personal computer that can be connected to a communication line may be used.

Embodiment 2

Figure 4:
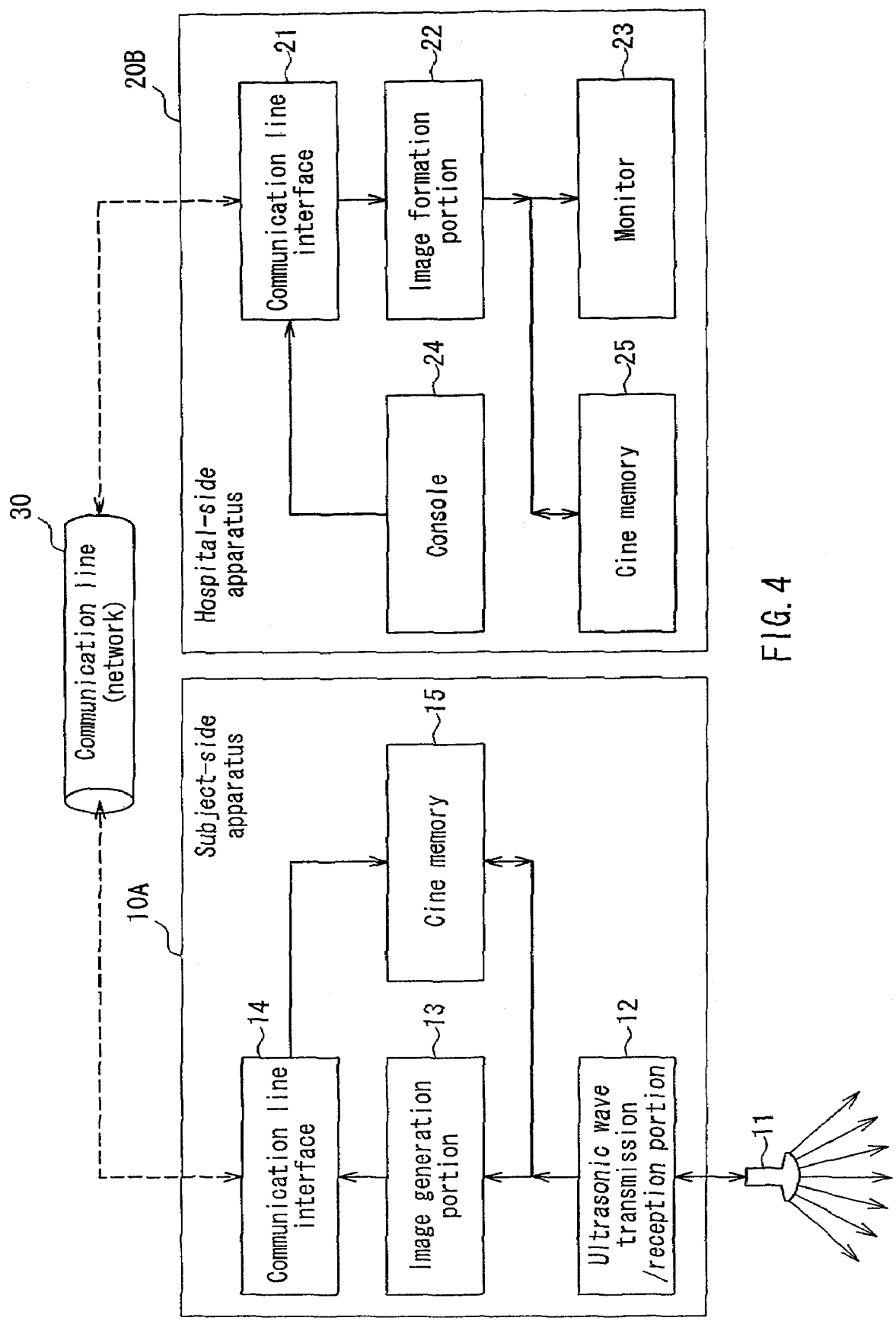
FIG. 4 is a block diagram schematically showing an example of a configuration of a remote ultrasonic diagnostic system according to Embodiment 2 of the present invention.

FIG. 4 is a block diagram schematically showing an example of a configuration of a remote ultrasonic diagnostic system according to Embodiment 2 of the present invention. Herein, the same reference numerals are assigned to the same elements as those composing the system shown in FIG. 1 so as to simplify their explanations. In the present embodiment, a cine memory 25 (a cine memory of an examiner-side apparatus) is provided also in a hospital-side apparatus 20B.

In the system of FIG. 4, when the console 24 of the hospital-side apparatus 20B requires to freeze, an ultrasonic image displayed on the monitor 23 freezes. At the same time, the communication line interface 21 transmits freeze information to the subject-side apparatus 10A via the communication line 30, and requires to retransmit the image data accumulated in the cine memory 15, whereby the data accumulated in the cine memory 15 is transmitted to the cine memory 25 in the hospital-side apparatus 20B via the image generation portion 13, the communication line interface 14 and the communication line 30, and is stored in the cine memory 25 in the hospital-side apparatus 20B. At this time, it is preferable to retransmit the data in the background without changing the image displayed on the monitor 23.

When the console 24 requests the cine-memory reproduction after completing the transmission of the image information, even if the image lacks a frame in a live mode, all of the frames are already retransmitted to the cine memory 25 after the freezing, and thus a cine-memory image can be reproduced and displayed on the monitor 23 with no missing frame.

As mentioned above, according to the present embodiment, the hospital-side apparatus also is provided with a cine-memory function, receives (for example, in the background) information that is accumulated in the cine memory 15 of the subject-side apparatus from the time immediately after the freezing, and accumulates the information in the cine memory 25 of the hospital-side apparatus. Thereby, even when the communication line between the subject side and the hospital side is disconnected due to a deterioration of the condition of the line, the hospital-side apparatus 20B alone can continue a diagnosis by the cine-memory reproduction and display with no missing frame.

Embodiment 3

Figure 5:
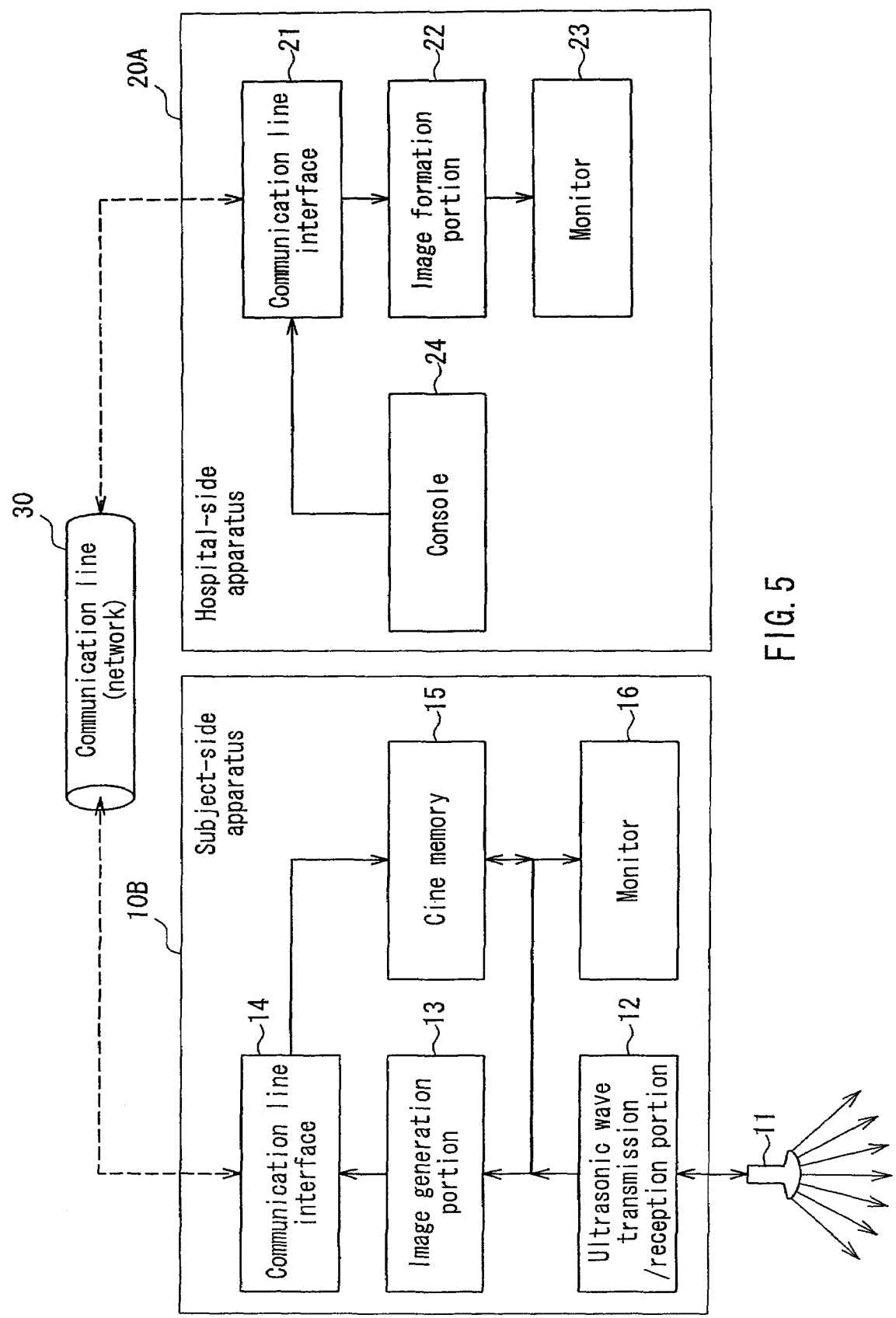
FIG. 5 is a block diagram schematically showing an example of a configuration of a remote ultrasonic diagnostic system according to Embodiment 3 of the present invention.

FIG. 5 is a block diagram schematically showing an example of a configuration of a remote ultrasonic diagnostic system according to Embodiment 3 of the present invention. In the present embodiment, a monitor 16 (a displaying means of a subject-side apparatus) is provided also in a subject-side apparatus 10B.

In the system of FIG. 5, similarly to Embodiment 1, in the case where the console 24 requests cine-memory reproduction, a designated frame is retransmitted from the cine memory 15 in the subject-side apparatus 10B in which an image frame is recorded to the communication line interface 21 of the hospital-side apparatus 20A without depending on a condition of the communication line 30, and is displayed on the monitor 23 via the image formation portion 22, whereby the cine memory can be reproduced without any frame missing from all of the 30 image frames per one second. At this time, the image that is transmitted to the hospital-side apparatus 20A is displayed also on the monitor 16 in the subject-side apparatus 10B.

As mentioned above, the present embodiment can provide an excellent remote ultrasonic diagnostic system that enables (an operator) on the subject side and (a medical doctor) on the hospital side to share diagnostic information by the same image, by displaying the frame that is requested to be retransmitted by the hospital-side apparatus 20A also on the monitor 16 of the subject-side apparatus 10B, when the frame is retransmitted to the hospital-side apparatus 20A.

Embodiment 4

Figure 6:
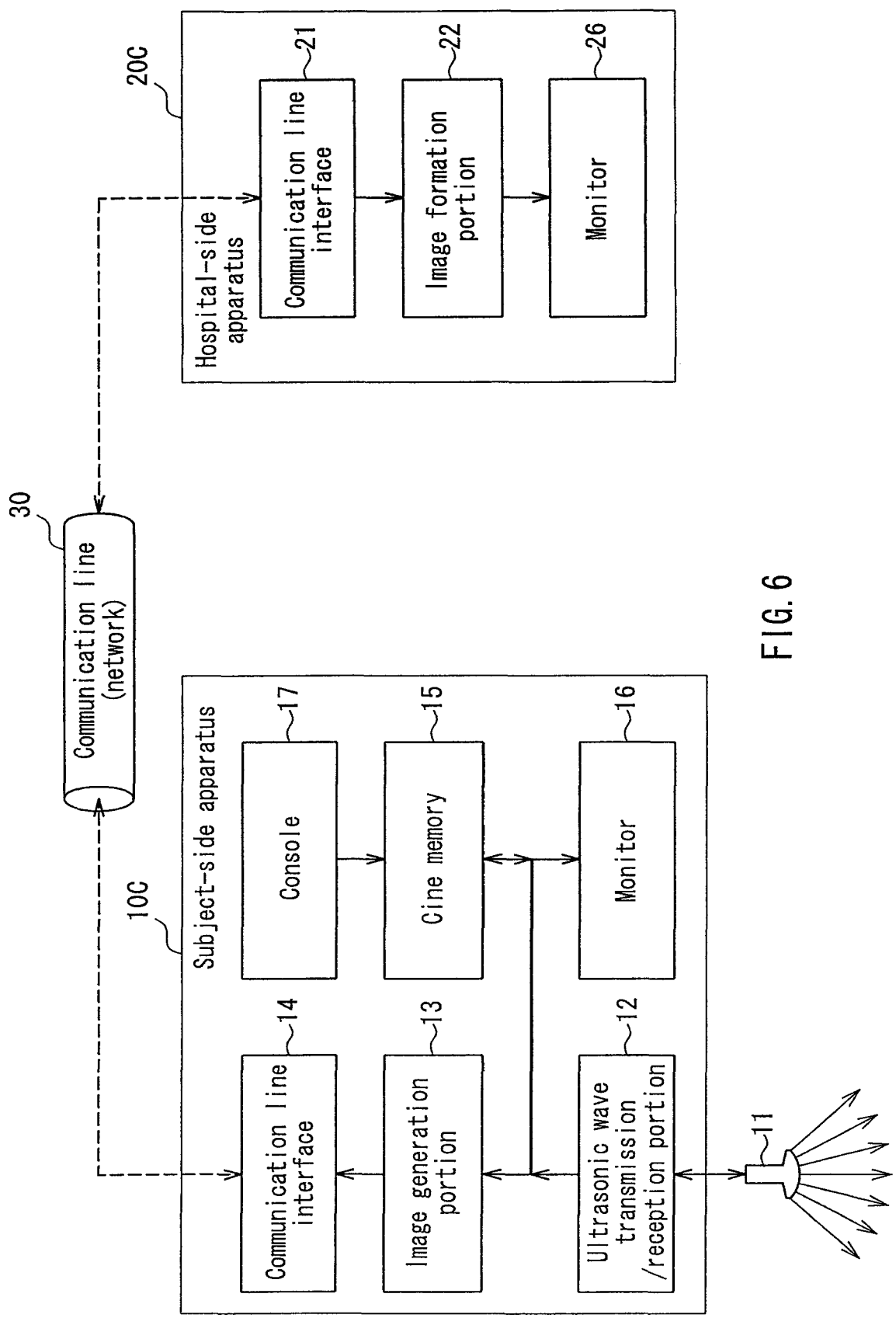
FIG. 6 is a block diagram schematically showing an example of a configuration of a remote ultrasonic diagnostic system according to Embodiment 4 of the present invention.

FIG. 6 is a block diagram schematically showing an example of a configuration of a remote ultrasonic diagnostic system according to Embodiment 4 of the present invention. In the present embodiment, a console 17 is provided in a subject-side apparatus 10C.

In the system of FIG. 6, in the case where the console 17 in the subject-side apparatus 10C requires cine-memory reproduction after freezing, a designated frame is transmitted from the cine memory 15 to a hospital-side apparatus 20C automatically. At this time, the frame that is displayed on the monitor 16 in the subject-side apparatus 10C is retransmitted to the communication line interface 21 of the hospital-side apparatus 20C, and is displayed on the monitor 26 via the image formation portion 22.

By retransmitting the frame, which is displayed on the monitor 16 of the subject-side apparatus 11C and is requested to be retransmitted, to the hospital-side apparatus 20C, and by displaying the frame also on the monitor 26 of the hospital-side apparatus 20C, the excellent remote ultrasonic diagnostic system that enables (an operator on) the subject side and (a medical doctor on) the hospital side to share diagnostic information by the same image can be provided.

Embodiment 5

Figure 7:
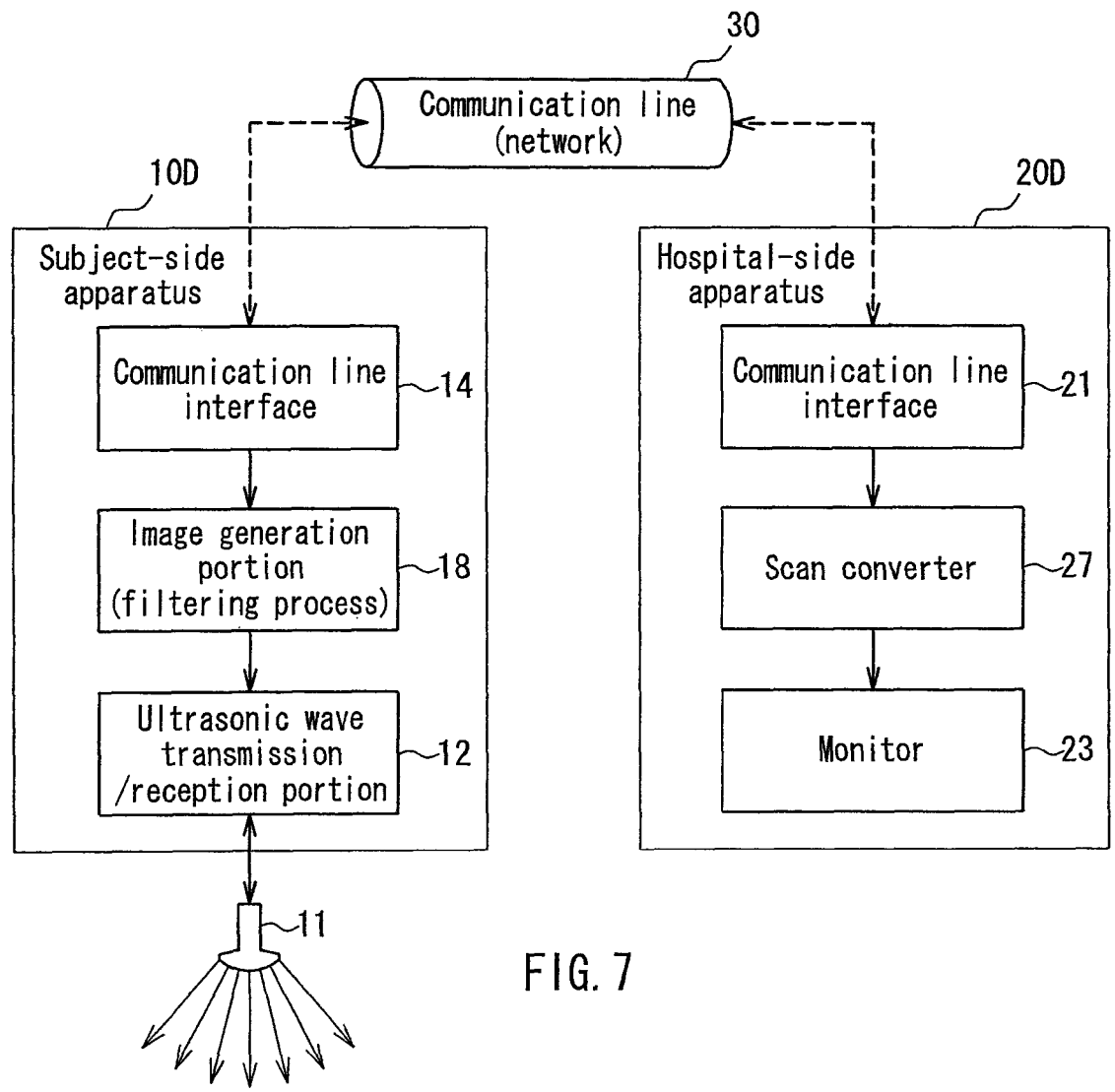
FIG. 7 is a block diagram schematically showing an example of a configuration of a remote ultrasonic diagnostic system according to Embodiment 5 of the present invention.

FIG. 7 is a block diagram schematically showing an example of a configuration of a remote ultrasonic diagnostic system according to Embodiment 5 of the present invention. In FIG. 7, a transmission pulse that is generated by the ultrasonic wave transmission/reception portion 12 in a subject-side apparatus 10D drives the ultrasonic probe 11 of a 128 ch type, and an ultrasonic signal is transmitted from the ultrasonic probe 11 into the subject and reception of the ultrasonic signal starts at the same time. The received ultrasonic signal is subjected to delay synthesis at the ultrasonic wave transmission/reception portion 12, then subjected to a filtering process (or a resampling process) by the image generation portion 18, and then is converted into ultrasonic image data in a number of sets of data that is optimized for scan conversion. The ultrasonic image data that is subjected to the filtering process by the image generation portion 18 is transmitted from the communication line interface 14 to the communication line 30.

The communication line interface 21 in the hospital-side apparatus 20D receives the ultrasonic image data that is transmitted via the communication line 30, and the received ultrasonic image data is input into a scan converter 27 (a scan-converting means of the examiner-side apparatus). The scan converter 27 shapes the ultrasonic image data into a form of a screen that coincides with a physical shape of the ultrasonic probe 11, and allows the monitor 23 to display the ultrasonic image.

Here, assuming the case of transmitting an unprocessed video output image of a general ultrasonic diagnostic apparatus to a hospital in a remote location via a communication line, in order to display a monochrome video signal of an NTSC standard on the monitor 23 of the hospital-side apparatus 20D, at least 8-bit monochrome data of a VGA size (640 pixels×480 lines) of 30 frames/second is necessary. Therefore, as represented by Formula 1 below, a data rate of about 74 Mbps in effective speed is necessary, and thus it is found that the data information amount is too large to be transmitted/received via a general communication line. Accordingly, a high-efficiency image compressing means such as an MPEG is necessary.

$$640\times480\times30\times8=73.7 \text{ Mbps} \qquad \text{Formula 1}$$

Here, the present embodiment focuses on a role of the scan converter in the ultrasonic diagnostic apparatus, and can decrease the information amount of the image data to be transmitted/received to be a minimum limit.

More specifically, the scan converter performs various interpolating processes to prevent the missing of an image and the generation of a unnatural discontiguous part at the time of displaying the image on the monitor, and provides the image that is most suitable for a medical diagnosis. On the other hand, the scan converter increases an apparent information amount significantly. Thus, by providing the scan converter 27 in the hospital-side apparatus 20D as shown in FIG. 7, the data rate that is transmitted/received in the communication line 30 can be decreased significantly.

Figure 8:
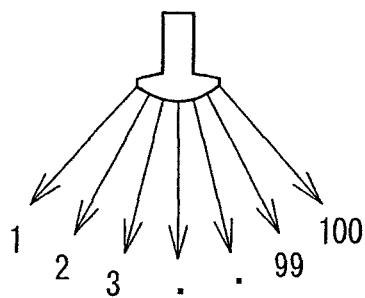
FIG. 8 is a schematic diagram showing an example of the number of acoustic scanning lines of the ultrasonic probe of FIG. 1 when sweeping at a single density.
Figure 9:
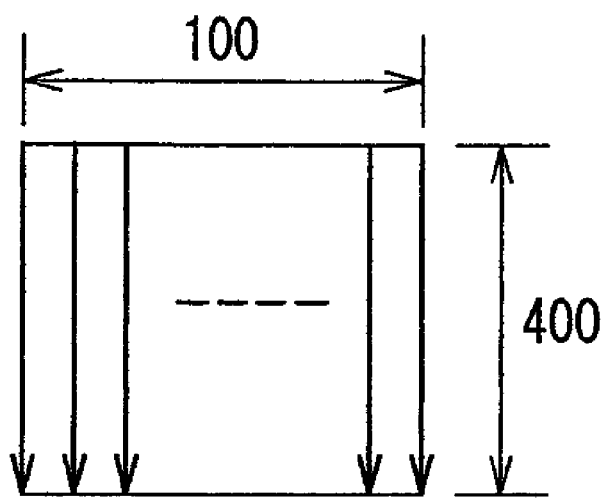
FIG. 9 is a schematic diagram showing an example of the number of sets of image data to be input into the scan converter of FIG. 1.
Figure 10:
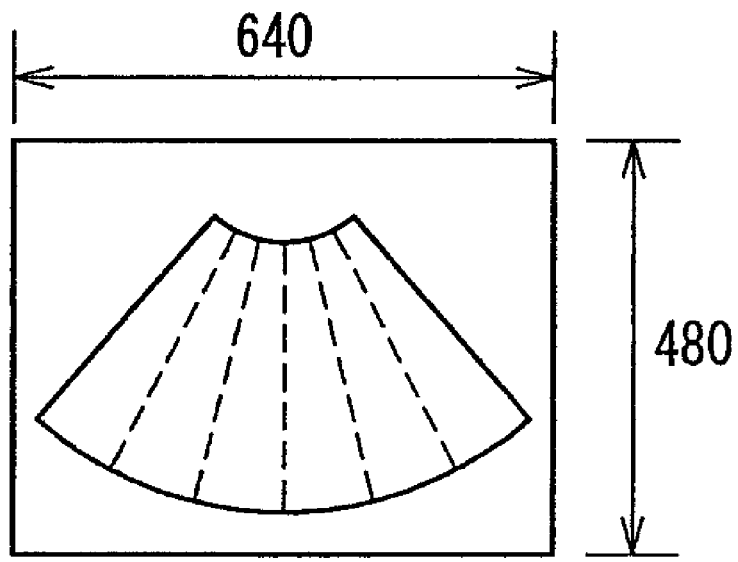
FIG. 10 is a schematic diagram showing an example of an ultrasonic image of a VGA size that is displayed on the monitor of FIG. 1.

For example, in the case of connecting the ultrasonic probe 11 of a 128 ch type to the subject-side apparatus 10D, the number of acoustic scanning lines is about 100 when sweeping at a normal single density, as shown in FIG. 8. Thus, the number of sets of the image data to be input into the scan converter 27 is 100 that is the same as the number of the acoustic scanning lines, and furthermore, the number of sets of the image data per each frame that is output from the image generation portion 18 and is input into the communication line interface 14 also is 100, as shown in FIG. 9. Similarly, the number of sets of the image data per each frame that is received by the communication line interface 21 of the hospital-side apparatus 20D also is 100. The scan converter 27 shapes these 100 sets of the image data into a form of a screen that coincides with a physical shape of the probe, and allows the monitor 23 to display one frame of the ultrasonic image of a VGA size as shown in FIG. 10.

Moreover, in the case where the image to be displayed on the monitor has a VGA size (640 pixels×480 lines), a suitable depth of the image data to be input into the scan converter 27 is about 400 dots, and thus a data rate required for transmitting/receiving 8-bit data of 30 frames/second is about 10 Mbps in effective speed, as represented by Formula 2 below.

$$100 \times 400 \times 30 \times 8 = 9.6 \text{ Mbps} \qquad \text{Formula 2}$$

Therefore, it is found that, according to the configuration of FIG. 7 that transmits/receives a necessity minimum of the information amount, an effect that is equivalent to the case of compressing the information amount to be 1/7 or less can be obtained automatically, and thus the uncompressed image sufficiently can be transmitted via a high-speed communication line. Furthermore, since a circuit (or a software) designed specifically for image compression is not required, no time lag for image compression is generated, and it is possible to provide the excellent ultrasonic diagnostic system, in which the image data without any compression nor any image degradation is input into the scan converter 27.

So far, the example of the monochrome mode is described. Whereas, in the case of a color Doppler mode, a color video signal is displayed on the monitor 23 of the hospital-side apparatus 20D, where 24-bit data of 30 frames/second is necessary for displaying the color video signal of the same image size, and thus a data rate of about 221 Mbps in effective speed is necessary as represented by Formula 3 below.

$$640 \times 480 \times 30 \times 24 = 221.2 \text{ Mbps} \qquad \text{Formula 3}$$

However, since a frame rate of a ultrasonic diagnostic apparatus in a color mode generally is lower than that in a monochrome mode, the data rate of the image data immediately before being input into the scan converter 27 does not change (or is decreased), and thus the data rate does not increase to about 10 Mbps or more in effective speed that is represented by Formula 2. That is, in the color Doppler mode, an effect equivalent to that of the case of compressing the image data to about 1/23 can be obtained, as represented by Formula 4 below.

$$9.6 \text{ Mbps}/221.2 \text{ Mbps} = 1/23 \qquad \text{Formula 4}$$

Figure 11:
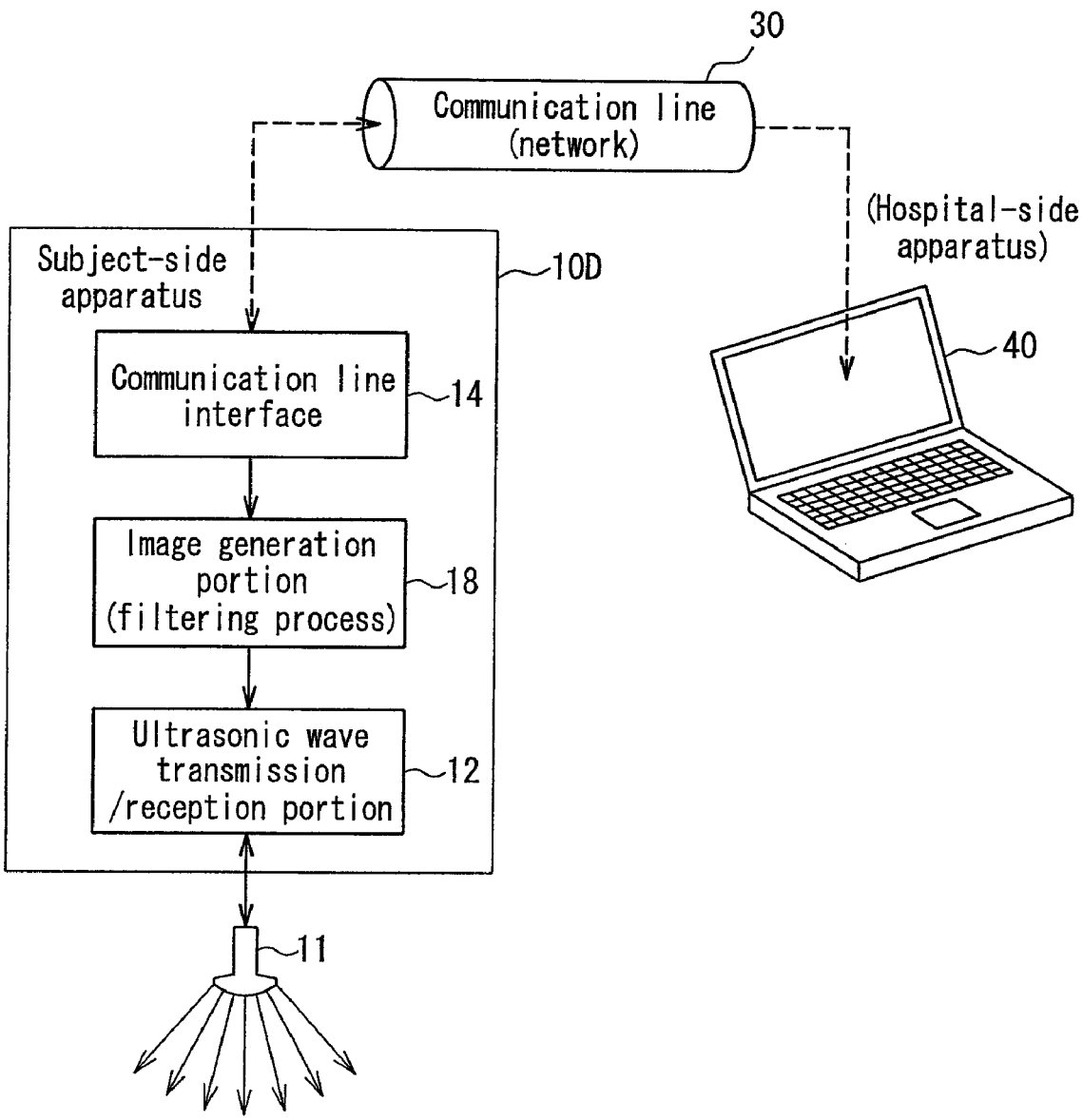
FIG. 11 is a block diagram schematically showing a modified example of the remote ultrasonic diagnostic system according to Embodiment 5, in the case of using a personal computer as a hospital-side apparatus.

Moreover, FIG. 11 shows an example of using a personal computer as the hospital-side apparatus. In recent years, image processing capabilities of personal computers have made remarkable progress, and thus a scan converter portion of an ultrasonic diagnostic apparatus can be formed only by software. Moreover, a function of connecting to a communication line (network) also is standard equipment.

Thus, by mounting the function of connecting to the communication line 30 and a scan converter function as software in a general personal computer 40, the hospital-side apparatus can be replaced by one set of the personal computer 40. That is, the excellent remote ultrasonic diagnostic system that does not require any specific hardware and has a large merit in terms of the cost can be provided.

Embodiment 6

Figure 12:
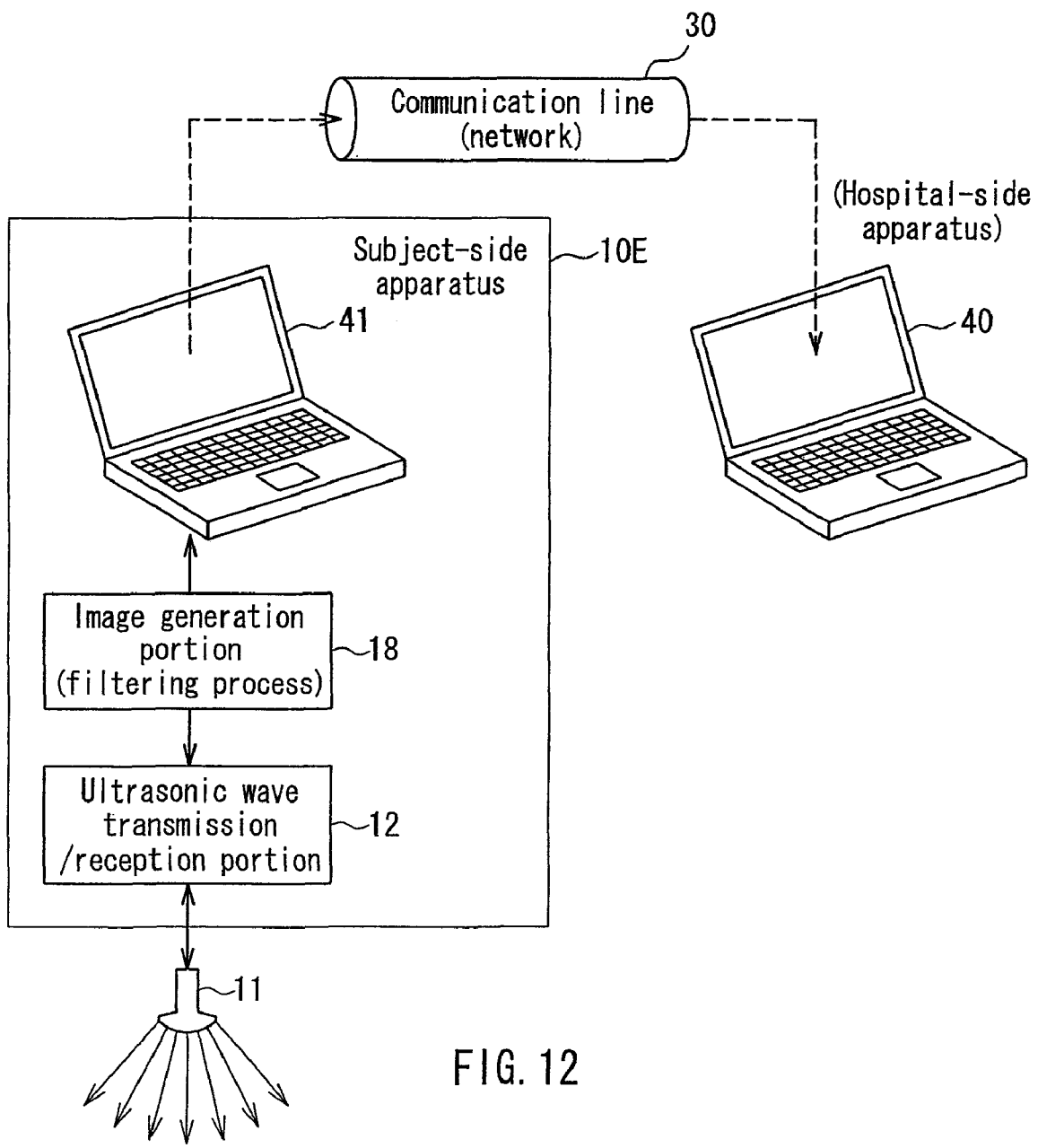
FIG. 12 is a block diagram schematically showing an example of a configuration of a remote ultrasonic diagnostic system according to Embodiment 6 of the present invention.

FIG. 12 is a block diagram schematically showing an example of a configuration of a remote ultrasonic diagnostic system according to Embodiment 6 of the present invention. The received ultrasonic signal is subjected to delay synthesis at the ultrasonic wave transmission/reception portion 12, then is subjected to a filtering process by the image generation portion 18, and then is converted into ultrasonic image data in a number of sets of data that is optimized for scan conversion. The ultrasonic image data that is subjected to the filtering process by the image generation portion 18 is input into a personal computer 41 in which the function of connecting to the communication line 30 is carried out by the software (the communication line interface, the scan converting means and the displaying means of the subject-side apparatus), and is transmitted to the communication line (network) 30 such as an internet and a LAN.

If the scan converter function also is carried out by a software in the personal computer 41 at the same time, a screen of the personal computer 41 on the subject side can display a real-time ultrasonic dynamic image that is the same as the ultrasonic image displayed on the personal computer 40 as the hospital-side apparatus, thereby enabling to provide the excellent remote ultrasonic diagnostic system that enables (an operator on) the subject side and (a medical doctor on) the hospital side to share diagnostic information.

Embodiment 7

Figure 13:
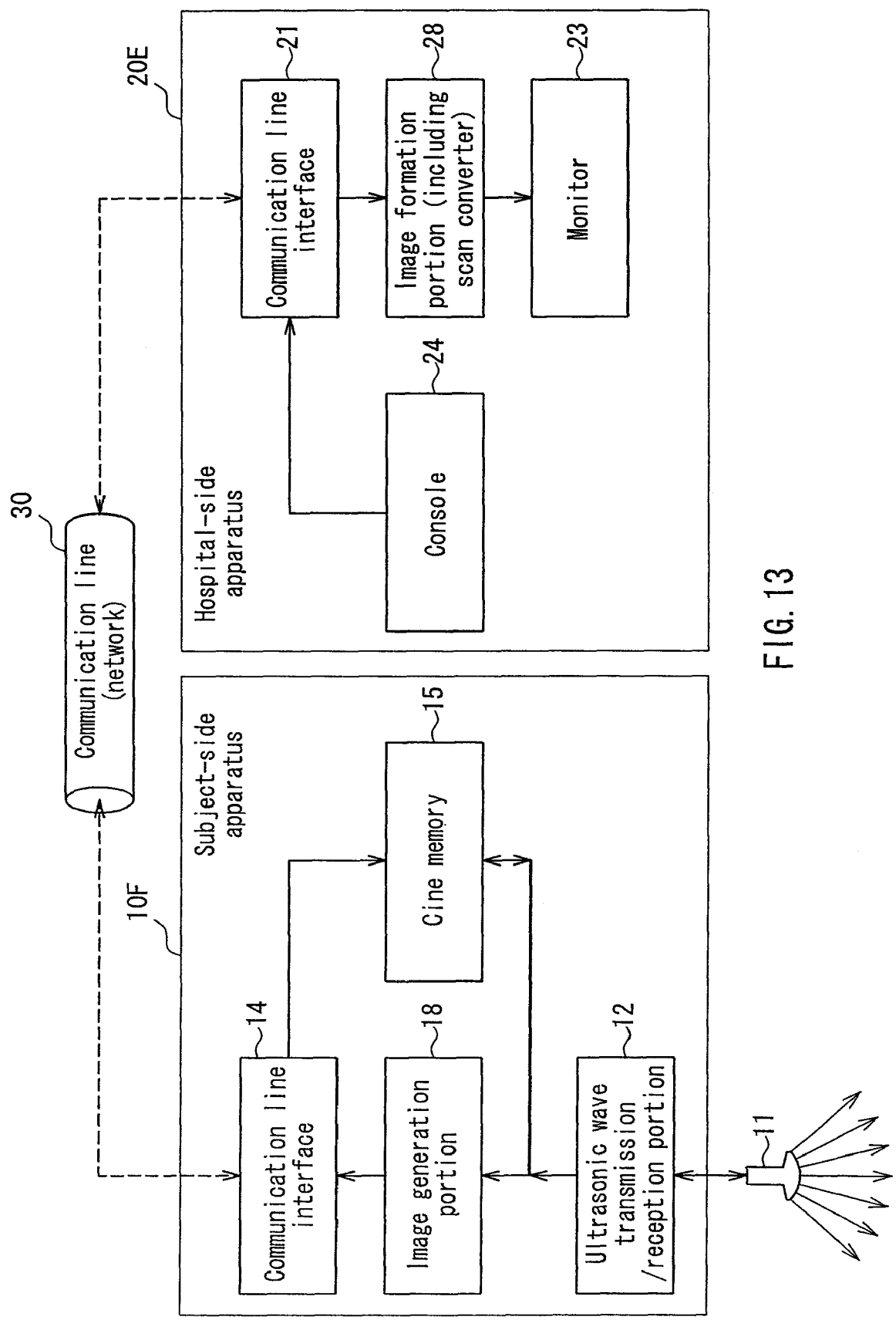
FIG. 13 is a block diagram schematically showing an example of a configuration of a remote ultrasonic diagnostic system according to Embodiment 7 of the present invention.

FIG. 13 is a block diagram schematically showing an example of a configuration of a remote ultrasonic diagnostic system according to Embodiment 7 of the present invention. This embodiment includes a configuration of combining Embodiment 1 shown in FIG. 1 and Embodiment 5 shown in FIG. 7. An image formation portion 28 in a hospital-side apparatus 20E includes a scan converter for converting the number of scanning lines of an ultrasonic image data of a transmitted frame. Specific actions of the cine memory 15 and the scan converter are as described above in the respective embodiments. The ultrasonic image data of the frame that is retransmitted from the cine memory 15 is processed similarly to the above-described case of using the scan converter.

In addition, the subject-side apparatuses and the hospital-side apparatuses that respectively are described in the above embodiments may be used in any combinations. Moreover, the communication line (network) may be a specific LAN in the hospital, or may be connected to an internet network by a general TCP/IP protocol. Needless to say, the image data can be relayed intermediately by a server function, and, if a plurality of the hospital-side apparatuses are connected thereto, many medical doctors can perform diagnoses at the same time, an moreover, the examiner-side apparatuses can achieve the same remote diagnoses even when they are located physically apart from each other. Whereas, if the subject-side apparatus and the hospital-side apparatus are connected directly by one-to-one by, for example, a cross cable for Ethernet (registered trademark), a similar effect can be obtained. Moreover, a further effect can be obtained, by recording a video image as the image data to be recorded in the cine memory, or adding an image compression and image elongation function such as an MPEG to each apparatus.

In addition, in each embodiment of the present invention, the remote ultrasonic diagnostic system was exemplified for explanation, however, the present invention also can be applied to other imaging devices for medical application (for example, X-ray CT scanners, magnetic resonance imaging (MRI) apparatuses and nuclear magnetic diagnostic apparatuses).

INDUSTRIAL APPLICABILITY

The remote ultrasonic diagnostic system of the present invention has an advantage of displaying an ultrasonic image with sufficiently suppressed degradation of an image quality compared with the image quality of an original image, even at a low data rate of a communication line, when an examiner performs a diagnosis with respect to a subject in a remote location via the communication line. Thus, the remote ultrasonic diagnostic system of the present invention can be applied usefully to a network system between an inside and an outside of a hospital, an inter-hospital network system and the like that enable many medical doctors to perform diagnoses at the same time.

The invention claimed is:

1. A remote ultrasonic diagnostic examiner-side apparatus that is used in a remote ultrasonic diagnostic system, comprising: an examiner-side apparatus by which an examiner performs a diagnosis with respect to a subject in a remote location via a communication line by using an ultrasonic image; and the subject-side apparatus on the subject side, the examiner-side apparatus comprising:
  a communication line interface that receives, during a live mode, an ultrasonic image data in real time that is transmitted via a communication line, and requests, during a mode after freezing, a communication line interface of the subject-side apparatus to retransmit a frame to be reproduced via the communication line;
  an image formation portion that forms an ultrasonic image using the ultrasonic image data received in real time or the retransmitted frame; and
  a displaying means that displays the ultrasonic image that is formed by the image formation portion,
  wherein during the mode after freezing, the ultrasonic image displayed by the display means is frozen to be a still state, and the request to the communication line interface of the subject-side apparatus to retransmit a frame occurs every time when a frame to be reproduced is designated by moving a pointer.

2. A remote ultrasonic diagnostic system in which a remote ultrasonic diagnostic subject-side apparatus and the remote ultrasonic diagnostic examiner-side apparatus according to claim 1 are connected via a communication line, the subject-side apparatus comprising:
  an ultrasonic wave transmission/reception portion that transmits an ultrasonic echo that is generated from an electroacoustic converting means driven by a transmission pulse, and receives an ultrasonic echo reflected by an inside of the subject;
  an image generation portion that generates ultrasonic image data from an ultrasonic signal that is received by the ultrasonic wave transmission/reception portion;
  a cine memory that sequentially stores the ultrasonic signal that is received by the ultrasonic wave transmission/reception portion per each frame; and
  a communication line interface that transmits the ultrasonic image data generated at the image generation portion via a communication line, and reproduces, from the cine memory, the frame that is requested to be retransmitted by the examiner-side apparatus after freezing, and retransmits the frame to the examiner-side apparatus via the communication line.

3. A remote ultrasonic diagnostic examiner-side apparatus that is used in a remote ultrasonic diagnostic system, comprising: an examiner-side apparatus by which an examiner performs a diagnosis with respect to a subject in a remote location via a communication line by using an ultrasonic image; and the subject-side apparatus on the subject side, the examiner-side apparatus comprising:
  a communication line interface that receives, during a live mode, an image data in real time that is transmitted via a communication line, and receives, during a mode after freezing, a frame that is retransmitted from a communication line interface of the subject-side apparatus via the communication line;
  an image formation portion that forms an ultrasonic image using the ultrasonic image data received in real time or the retransmitted frame; and
  a displaying means that displays the ultrasonic image that is formed by the image formation portion,
  wherein during the mode after freezing, the ultrasonic image displayed by the display means is frozen to be a still state, and the request to the communication line interface of the subject-side apparatus to retransmit a frame occurs every time when a frame to be reproduced is designated by moving a pointer.

4. A remote ultrasonic diagnostic system in which a remote ultrasonic diagnostic subject-side apparatus and the remote ultrasonic diagnostic examiner-side apparatus according to claim 3 are connected via a communication line, the subject-side apparatus comprising:
  an ultrasonic wave transmission/reception portion that transmits an ultrasonic echo that is generated from an electroacoustic converting means driven by a transmission pulse, and receives an ultrasonic echo reflected by an inside of the subject;
  an image generation portion that generates ultrasonic image data from an ultrasonic signal that is received by the ultrasonic wave transmission/reception portion;
  a cine memory that sequentially stores the ultrasonic signal that is received by the ultrasonic wave transmission/reception portion per each frame;
  a displaying means that reproduces, from the cine memory, the frame that is requested to be retransmitted in the subject-side apparatus after freezing, and displaying the frame as an ultrasonic image; and
  a communication line interface that transmits the ultrasonic image data generated at the image generation portion via a communication line, and retransmits the frame that corresponds to the ultrasonic image displayed on the displaying means to the examiner-side apparatus via the communication line.

5. A remote ultrasonic diagnostic examiner-side apparatus that is used in a remote ultrasonic diagnostic system, comprising: an examiner-side apparatus by which an examiner performs a diagnosis with respect to a subject in a remote location via a communication line by using an ultrasonic image; and the subject-side apparatus on the subject side, the examiner-side apparatus comprising:
  a communication line interface that receives, during a live mode, an image data in real time that is transmitted via a communication line, and requests, during a mode after freezing, a communication line interface of the subject-side apparatus to retransmit a frame to be reproduced via the communication line;
  an image formation portion that comprises a scan converting means that converts the number of scanning lines of an ultrasonic image data of the ultrasonic image data received in real time or the retransmitted frame, and forms an ultrasonic image by the scan converting means; and a displaying means that displays the ultrasonic image that is formed by the image formation portion, wherein during the mode after freezing, the ultrasonic image displayed by the display means is frozen to be a still state, and the request to the communication line interface of the subject-side apparatus to retransmit a frame occurs every time when a frame to be reproduced is designated by moving a pointer.

6. A remote ultrasonic diagnostic system in which a remote ultrasonic diagnostic subject-side apparatus and the remote ultrasonic diagnostic examiner-side apparatus according to claim 5 are connected via a communication line, the remote ultrasonic diagnostic examiner-side apparatus comprising:

the subject-side apparatus comprising:

an ultrasonic wave transmission/reception portion that transmits an ultrasonic echo that is generated from an electroacoustic converting means driven by a transmission pulse, and receives an ultrasonic echo by being reflected by an inside of the subject;

an image generation portion that generates ultrasonic image data by performing a filtering process with respect to an ultrasonic signal that is received by the ultrasonic wave transmission/reception portion;

a cine memory that sequentially stores the ultrasonic signal that is received by the ultrasonic wave transmission/reception portion per each frame; and a communication line interface that transmits the ultrasonic image data generated at the image generation portion via a communication line, and reproduces, from the cine memory, the frame that is requested to be retransmitted by the examiner-side apparatus after freezing, and retransmits the frame to the examiner-side apparatus via the communication line.

* * * * *

UNITED STATES PATENT AND TRADEMARK OFFICE
CERTIFICATE OF CORRECTION

| | |
|---|---|
| PATENT NO. | : 7,905,834 B2 |
| APPLICATION NO. | : 10/597660 |
| DATED | : March 15, 2011 |
| INVENTOR(S) | : Watanabe et al. |

It is certified that error appears in the above-identified patent and that said Letters Patent is hereby corrected as shown below:

Title page, Item (75)
Inventors: "Yoshinobu Watanabe, Kadoma (JP)" should read --Yoshinobu Watanabe, Kanagawa (JP)--.

Signed and Sealed this
Fourteenth Day of June, 2011

David J. Kappos
*Director of the United States Patent and Trademark Office*